United States Patent [19]
Sordillo et al.

[11] Patent Number: 5,124,145
[45] Date of Patent: Jun. 23, 1992

[54] METHOD FOR THE PREVENTION AND TREATMENT OF BOVINE MASTITIS

[75] Inventors: Lorraine M. Sordillo; Lorne A. Babiuk, both of Saskatoon, Canada

[73] Assignee: Ciba-Geigy Canada Ltd., Mississauga, Canada

[21] Appl. No.: 426,287

[22] Filed: Oct. 24, 1989

[51] Int. Cl.$^5$ .............................................. A61K 37/66
[52] U.S. Cl. .................................. 424/85.5; 424/85.4; 514/885; 514/889
[58] Field of Search ........................... 424/85.4, 85.5; 514/885, 889

[56] References Cited

U.S. PATENT DOCUMENTS 4,083,959  4/1978  Homma et al. ..................... 424/92

FOREIGN PATENT DOCUMENTS 0242233  10/1987  European Pat. Off.

OTHER PUBLICATIONS

Sordillo et al., *Int. J. Biochem.*, (1987), 19(12):1165–1172.
Sordillo et al., *Am. J. Vet. Res.*, (1988), 49(7):1112–1120.
Paape et al., *International Symposium on the Ruminant Immune System*, Plymouth, N.H., (1980), J. E. Butler, ed., Plenum Press, New York, pp. 555–578.
Nagahata et al., *J. Vet. Med.*, (1988), 35:747–751.
Nickerson et al., *J. Diary Sci.*, (1989), 72(6):1665–1678.
Hill, *Res. Vet. Sci.*, (1981), 31:71–112.
Ohmann et al., *J. Interferon Res.*, (1986), 6:123–136.
Trinchieri et al., *Immunol. Today*, (1985), 6(4):131–136.
Billiau, *J. Interferon Res.*, (1987), 7:559–567.
Frost et al., *Australian Vet. J.*, (1986), 63(10):327–331.
Hershman et al., *Clin. Exp. Immunol.*, (1988), 72:406–409.
Hershman et al., *J. Interferon Res.*, (1988), 8:367–373.
Hill et al., *Res. Vet. Sci.*, (1984), 37:179–187.
Jensen et al., *Cell. Immunol.*, (1988), 117:369–377.
McDonald et al., *Am. J. Vet. Res.*, (1981), 42(2):229–231.
Shemer et al., *Interferon and Nonviral Pathogens*, (1988), G. I. Byrne et al., eds., Marcel Dekker, Inc., New York, pp. 73–94.
van Dissel et al., *J. Immunol.*, (1987), 139(5):1673–1678.
Lawman et al., "Comprehensive Biotechnology", (1989), Permagon Press, London, Chapter 4, pp. 64–106.
Hershman et al., "Modulation of Infection by Gamma Interferon Treatment Following Trauma", *Infect. Immun.*, (1988), 56(9).

*Primary Examiner*—Frederick E. Waddell
*Assistant Examiner*—Raymond J. Henley, III
*Attorney, Agent, or Firm*—Morrison & Foerster

[57] ABSTRACT

A method for treating or preventing mastitis in cows is disclosed. The method contemplates the intramammary injection of bovine interferon-gamma. Interferon-gamma can be administered prior to infection to effectively suppress the rate, severity, and duration of subsequent bacterial infection, or can be administered subsequent to infection to effectively treat mastitis.

9 Claims, 3 Drawing Sheets

METHOD FOR THE PREVENTION AND TREATMENT OF BOVINE MASTITIS

TECHNICAL FIELD

The present invention relates generally to the use of cytokines in the prevention of bacterial infections. More specifically, the instant invention pertains to the use of interferon-gamma in the prevention and treatment of bovine mastitis.

BACKGROUND OF THE INVENTION

The mammary gland has a natural ability to prevent bacterial invasion, but various physiological events can inhibit this capability. For example, the ability of mammary gland neutrophils to phagocytize mastitis-causing pathogens and suppress bacterial multiplication is critical to, the outcome of intramammary infection (Paape et al., 1979). Although both neutrophils and macrophages predominate in mammary secretions and tissues (Sordillo et al., 1987; Sordillo and Nickerson, 1988), evidence suggests that the antibacterial activities of these cells are reduced in the presence of mammary secretions and compromised during physiological transitions of the gland (Paape et al., 1981; Nagahata et al., 1988; Sordillo and Nickerson, 1988). Consequently, the bovine mammary gland is highly susceptible to mastitis immediately following the cessation of lactation and during the periparturient period (Nickerson, 1989). Incidence of clinical mastitis is highest during early lactation often resulting from new intramammary infections obtained during the nonlactating period. Increased susceptibility during these times is most likely due to a combination of increased exposure of teat ends to mastitis-causing pathogens and diminished host defense mechanisms, as described above, during functional transitions of the mammary gland.

Mastitis during the periparturient and early lactating periods is caused by a multitude of bacteria. Common etiological agents include *Escherichia coli* and *Staphylococcus sp*. Coliform infection is rare in middle and late lactation, but is most severe during the first few weeks of lactation where it is a major cause of acute toxic mastitis. Disparities in establishment and severity of, coliform mastitis with respect to stage of lactation have been explained by the rate of growth of the organism within the gland, the elaboration and absorption of toxins, and the varying susceptibility of the host during these stages. A rapid and intense inflammatory response in lactating tissue has been observed following experimental challenge with *E. coli* (Hill, 1981). In most cases, the bacteria were eliminated rapidly without causing damage to secretory parenchymal tissue. In contrast, quarters infected with *E. coli* during the immediate postpartum period had minimal neutrophil influx, which probably allows the unrestricted growth of the organism. The delayed diapedesis of neutrophils and slow inflammatory response within the gland may be a result of decreased sensitivity of alveolar and ductular epithelium to endotoxins during functional transitions of the gland.

Interferons (IFN) are a family of closely related proteins of three major types (Lawman et al., 1989). Interferons-alpha and -beta are produced by a variety of cell types in response to several inducers including viral infections, bacterial products and tumor cells. Interferon-gamma is predominantly produced by antigen- or mitogen-stimulated T-lymphocytes. In addition to the antiviral and antiproliferative activities, all classes of IFN are known to exhibit many immunomodulatory properties (Lawman et al., 1989).

IFN-gamma has been shown to be a potent immunomodulator and appears to enhance natural killer cell activity, antibody-dependent cellular cytotoxicity, and cytotoxic T-lymphocyte activity (Lawman et al., 1989). Interferon-gamma also enhances macrophage-mediated cytotoxicity against tumor cells, induces membrane-bound Fc receptors for IgG on macrophages, and stimulates the synthesis and release of reactive oxygen metabolites from both macrophages and neutrophils (Bielefeldt Ohmann and Babiuk, 1986; Trinchieri and Perussia, 1985).

The efficacy of interferons in the treatment of mastitis has not heretofore been studied to applicants' knowledge.

SUMMARY OF THE INVENTION

The present invention is based on the surprising discovery that interferons can protect dairy cattle against coliform mastitis.

In one embodiment the present invention is directed to a method of treating or preventing mastitis in a mammal comprising administering to said mammal a therapeutically effective amount of interferon.

In another embodiment, the instant invention is directed to a method for treating or preventing coliform mastitis in a cow comprising administering to said cow a therapeutically effective amount of bovine interferon-gamma. The administration can be done either before or after infection.

These and other embodiments of the present invention will readily occur to those of ordinary skill in the art in view of the disclosure herein.

DETAILED DESCRIPTION

Figure 1:
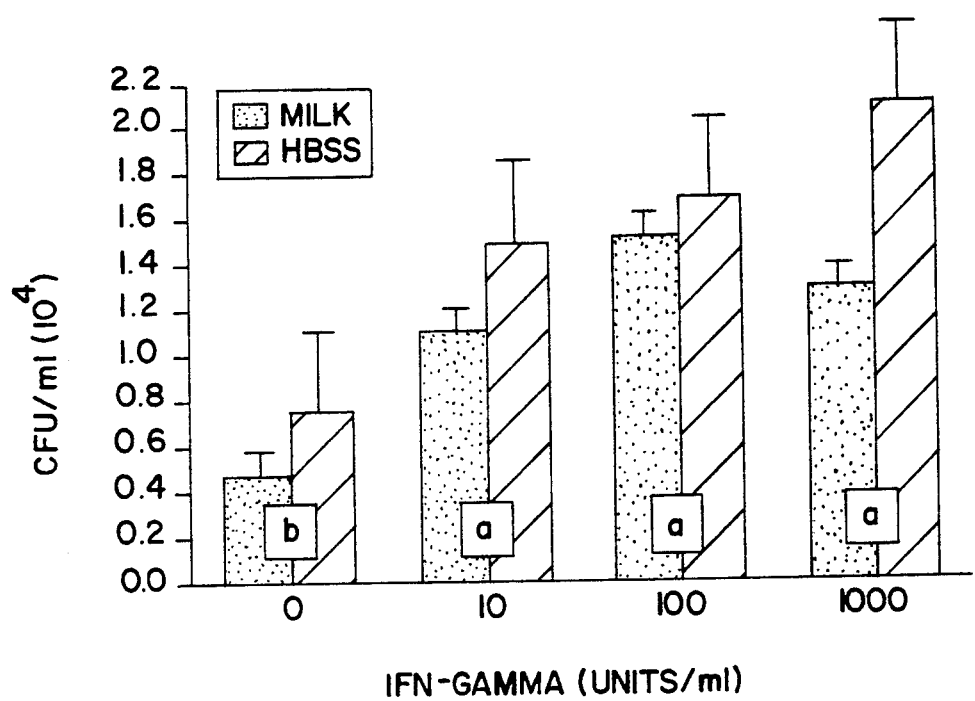
FIG. 1 depicts the effect of increasing IFN-gamma doses on bacterial phagocytosis of bovine mammary neutrophils pretreated with either periparturient mammary secretions (milk) or Hank's balanced saline solution (HBSS). Data are expressed as colony-forming units (CFU) of *Staphylococcus aureus* recovered from mammary neutrophils at t=0. Bars between IFN-gamma treatments with different letters (a,b) are significantly different ($P<0.05$).

The practice of the present invention will employ, unless otherwise indicated, conventional techniques of immunology, protein chemistry, biochemistry and molecular biology which are within the skill of the art. Such techniques are explained fully in the literature. See, e.g., *Handbook of Experimental Immunology*, Vols. I-IV (D. M. Weir and C. C. Blackwell eds., 1986, Blackwell Scientific Publications), and the series *Methods in Enzymology* (S. Colowick and N. Kaplan eds., Academic Press, Inc.)

The present invention is directed to the treatment or prevention of mastitis in mammals by the administration of one or more interferons to the subject mammal. A preferred embodiment of the invention is the treatment or prevention of coliform mastitis in cattle using bovine interferon (BoIFN)-gamma.

The present invention contemplates employing any form of human or BoIFN, either alone or in combination. Thus, the present invention encompasses using native forms of the interferons. Particularly surprising, however, is that recombinant forms of the interferons have sufficient biological activity to provide for effective treatment or prevention of mastitis. Since the production of recombinant interferon has substantial advantages relative to the purification of native polypeptides, recombinant interferons are a preferred embodiment. It is also contemplated that synthetic forms of human or BoIFN, and muteins or fragments of BoIFN, exhibiting effective biological activity, are also within the scope of the invention. A mutein of human or BoIFN is a polypeptide substantially homologous to the native protein, and more homologous to the bovine or human form than to IFNs from other species. A fragment of human or BoIFN is a polypeptide that is homologous to a region of sufficient length in the protein such that the sequence is unique to human or BoIFN.

The production of recombinant animal interferons, including alpha (leukocyte) and gamma (immune), is known in the art. See, e.g., EPO Pub. No. 088,622, by D. Capon & D. Goeddel. Furthermore, recombinant BoIFN-gamma is available commercially from Ciba-Geigy, Ltd., Basel, Switzerland.

As indicated, the present invention is concerned with treating or preventing mastitis. By "treating" is meant curing or ameliorating an animal that has contracted mastitis. "Preventing" mastitis means preventing the occurrence of the infection, or tempering the severity of the infection if it is later contracted.

Typically, the interferons of the present invention are administered by intramammary injection; however, effective dosages may be administered via intramuscular, subcutaneous, or intravenous injection. When prepared as injectables, the interferons are generally administered using a pharmaceutically acceptable vehicle or excipient. Suitable vehicles are, for example, water, saline, dextrose, glycerol, ethanol, or the like, and combinations thereof. In addition, if desired, the vehicle may contain auxiliary substances such as wetting or emulsifying agents or pH buffering agents. The active ingredient will typically range from about 1% to about 95% (w/w) of the composition administered, or even higher or lower if appropriate.

A "therapeutically effective amount" of interferon is a dose sufficient to either prevent or treat mastitis in a subject to which the interferon is administered. The dosages of the interferons which can treat or prevent mastitis can be determined in view of this disclosure by one of ordinary skill in the art by running routine trials with appropriate controls. Comparison of the appropriate treatment groups to the controls will indicate whether a particular dosage is effective in preventing or treating a disease used in a controlled challenge. In general, effective dosage will vary depending on the mode of administration. It has been found that in the case of an intramammary injection using recombinant BoINF-gamma, administration of $10^5$ U per quarter is sufficient to retard *E. coli* mastitis.

If administered intramuscularly, subcutaneously, or intravenously, effective dosages will depend on the weight of the animal and will typically run in the range of from about 0.1 ug/kg to about 40 ug/kg. More typically, the dosage will be at least about 1 ug/kg, but less than 10 ug/kg. On an absolute basis, single-dose formulations will contain from about 10 ug to about 1,000 ug. More typically, preferred single-dose formulations will be at least about 30 ug, 100 ug or even 200 ug, but usually no more than about 600 ug or 700 ug. Effective dosages are believed to fall within a relatively large range.

Beyond dosage, an effective administration of interferons according to the present invention will in part depend on the number and timing of the dosages. For example, multiple administrations of a dosage may be given to an animal, typically at least about 24 hours apart. In some circumstances it may be desirable to administer the interferon at least twice to the animal, or at least three times. It may even be desirable to administer even more dosages to the animal, such as six, seven, eight, or even nine over an equal number of days or longer. Again, it is believed that the precise combination of dosage and timing will be subject to a wide range of variation and that numerous combinations effective in treating or preventing a disease can be readily established by those of ordinary skill in the art in view of the present disclosure.

The interferons of the subject invention can be administered prior to infection, and thus serve as a prophylactic or can be given after the subject has shown signs of infection.

Described below are several examples illustrating the practice of the present invention. These examples are provided for illustrative purposes only, and are not intended to limit the scope of the appended claims.

EXPERIMENTAL

EXAMPLE 1

Preliminary experiments were performed to determine the effect of recombinant BoIFN on mammary neutrophil activity during the periparturient period.

Mammary Neutrophil Isolation

Neutrophils were isolated from the mammary gland of a heifer after intramammary injection of 5 ug of lipopolysaccharide (LPS) in 5 ml of HBSS. At 15 h after LPS administration, 30 ml of HBSS were injected into the LPS-treated quarter and mammary secretions were collected into a sterile polypropylene tube. Mammary neutrophils were purified by Ficoll-Hypaque density centrifugation. After 2 washings, the cells were resuspended in HBSS containing 5% fetal bovine serum (FBS) and filtered through a 30 um Nitex filter (Tetko Co., Elmsford, N.Y.). Separation of mammary leukocytes via this technique consistently resulted in a more than 96% neutrophil population. The percentage of viable cells was determined by hemacytometer count using trypan blue exclusion. Mammary neutrophils were cytocentrifuged onto poly-L-lysine-coated slides and stained with Wright,s stain for differential cell counts.

Pretreatment and Stimulation of Mammary Neutrophil

Mammary secretion samples from individual quarters (n=8) were collected from 2 cows at approximately 14 and 7 days prior (±2 days) to expected parturition (C-14 and C-7) and at parturition (C-0). Aseptic foremilk samples were collected in duplicate and used to determine infection status of each quarter. Bacteriologic evaluation of foremilk samples revealed that all quarters (n=8) were free of intramammary infection during the entire sampling period. Secretions were centrifuged for 30 min (3,000 g at 5° C.) to remove fat and cellular debris (skim milk).

Skim milk preparations (1 ml) from each sampling period were mixed with 1 ml of mammary neutrophils ($8 \times 10^6$ cells) and allowed to incubate for 1 h at room temperature. Control cells were incubated in HBSS. The mixture was washed in HBSS and separated into four 1-ml volumes containing $2 \times 10^6$ cells each. For each sampling period, skim milk-treated neutrophils were subsequently incubated with 10 U, 100 U and 1000 U of recombinant BoIFN-gamma (Ciba-Geigy Ltd., Basel, Switzerland) or HBSS for 2 h at room temperature. The cells were washed and resuspended in HBSS with 5% FBS to a final concentration of $1 \times 10^6$ cells/ml.

Phagocytic and Bacteriocidal Assay

Mammary neutrophil phagocytic and bactericidal capacities were evaluated using *Staphylococcus aureus* isolated from a clinical case of bovine mastitis. Bacteria in log phase growth were opsonized with bovine sera with an agglutination titer of 1/16 against *S. aureus*.

Opsonized *S. aureus* cells ($1 \times 10^6$ colony-forming cells (CFU) in 1 ml) were mixed with 1 ml of treated neutrophils ($1 \times 10^6$) and incubated (10 min, 37° C.) in a shaking water bath. After initial incubation, the mixtures were washed, resuspended in HBSS containing lysostaphin (Sigma Chemical Co., St. Louis, Mo.), and incubated for 30 min to remove extracellular bacteria. Cells were washed and divided into 3 aliquots: t=0 min, t=30 min, and t=60 min. Following the second incubation, PMN were washed, resuspended in 1 ml HBSS, and subjected to sonication.

The number of viable bacteria for each time period was estimated by a standard plate count method. The mean CFU of bacteria at t=0 was used as an index of phagocytosis. Bactericidal capacity (percent killing) was computed from:

$$1 - \frac{CFU \text{ bacteria}, t = 60}{CFU \text{ bacteria}, t = 0} \times 100$$

Chemiluminescence

Luminol-enhanced chemiluminescence was measured with a Packard Picolite luminometer (Packard Instrument Co., Downers Grove, Ill.). Treated neutrophils ($1 \times 10^6$ cells/100 ul) were added to vials containing 15 ul luminol, 200 ul of opsonized zymosan (10 mg/ml), and 1,685 ul HBSS. Vials were counted for 10 s at 7 min intervals for a total of 210 min. All assays were performed in duplicate. For each quarter, mammary secretion from all sampling periods and the appropriate controls were assayed on the same day.

Transmission Electron Microscopy

Mixtures containing skim milk-treated neutrophils, recombinant BoIFN-gamma, and *S. aureus* from one quarter were fixed in 2.5% glutaraldehyde in 0.1M cacodylate buffer for 2 h and postfixed in 0.1M cacodylate-buffered osmium tetroxide for 1.5 h. Following dehydration in a graded series of ethanol washes, cell pellets were embedded in epoxy resins. Ultrathin sections (60 nm) for electron microscopy were stained with 5% uranyl acetate in 50% methanol for 20 min followed by 0.4% lead citrate for 10 min. Sections were examined using a Philips 300 transmission electron microscope (Philips Export, Eindhoven, Netherlands) operating at 60 kV.

Statistical Analysis

Data were analyzed by least-squares analysis of variance using the general linear model procedure to determine effects of mammary secretion and increasing doses of recombinant BoIFN-gamma on mammary gland neutrophil function. Statistical analysis included effect of cow, mammary secretion, recombinant BoIFN-gamma, and interaction of mammary secretions with recombinant BoIFN-gamma. Preplanned comparisons of least square means from the overall model were made by pairwise t-test.

Results

The effects of periparturient mammary secretion of neutrophil function are shown in Table 1. Mammary neutrophils treated with secretions obtained during the last 2 weeks of gestation had significantly lower phagocytic and bactericidal activity when compared with control cells incubated in HBSS. Cells incubated with skim milk preparations also had significantly less production of reactive oxygen species (ROS) when compared with control neutrophils incubated in HBSS. Secretions obtained at C-7 and C-0 tended to inhibit neutrophil function more than secretions obtained at C-14.

Ultrastructural examination of skim-milk-treated neutrophils frequently revealed phagocytic vacuoles containing casein-like micelles and debris in addition to ingested bacteria. In contrast, control neutrophils incubated in HBSS primarily had internalized bacteria with very little ingested debris.

Figure 2:
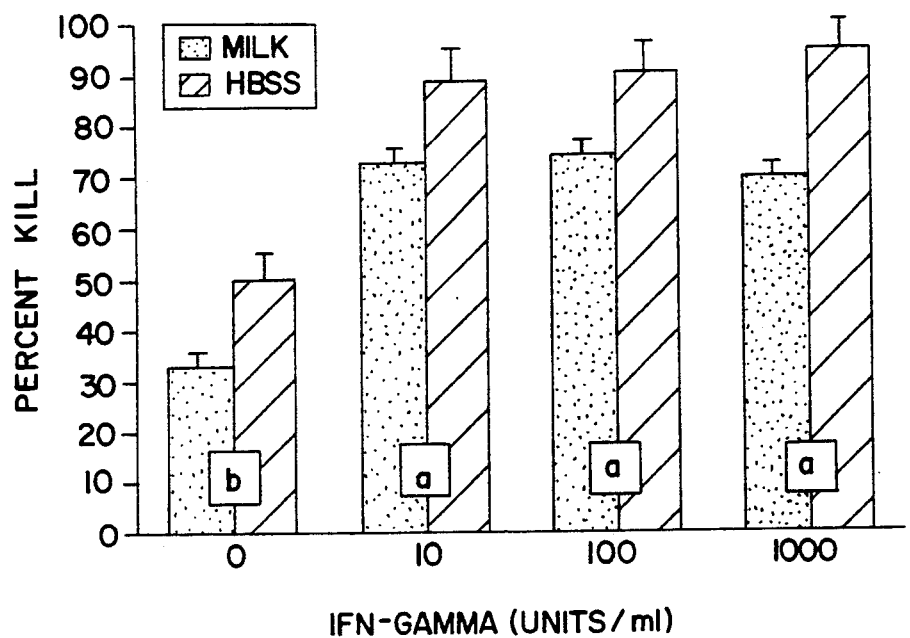
FIG. 2 shows the effect of increasing IFN-gamma doses on bactericidal activity of bovine mammary neutrophils pretreated with either periparturient mammary secretions (milk) or Hank's balanced saline solution (HBSS). Bars between IFN-gamma treatments with different letters (a,b) are significantly different ($P<0.05$).
Figure 3:
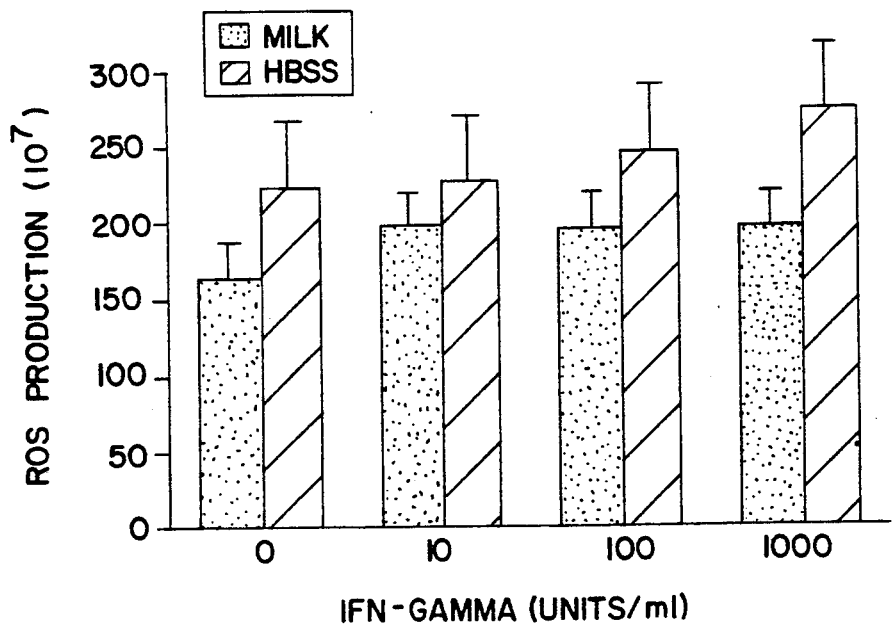
FIG. 3 demonstrates the effect of increasing IFN-gamma doses on the production or reactive oxygen species (ROS) by bovine mammary neutrophils pretreated with either periparturient mammary secretions (milk) or Hank's balanced saline solution (HBSS). Data are expressed as total area under the curve.

Treatment with recombinant BoIFN-gamma significantly increased the phagocytic and bactericidal capacity of neutrophils for *S. aureus* (FIGS. 1 and 2) for both skim milk-treated and control cells. However, skim milk-treated neutrophils consistently showed lower phagocytic and bactericidal capabilities when compared with cells incubated in HBSS. There were no significant effects of recombinant BoIFN-gamma on production of ROS by mammary neutrophils although values tended to be slightly higher following recombinant BoIFN-gamma treatment (FIG. 3).

There were no apparent dose-dependent responses of skim milk-treated neutrophils to increasing recombinant BoIFN-gamma concentrations for bacterial phagocytosis, bactericidal activity, of ROS generation. In contrast, HBSS-treated neutrophils showed a trend of enhanced response with increasing doses of recombinant BoIFN-gamma for all parameters measured (FIGS. 1-3).

TABLE 1

Effects of periparturient mammary secretions on polymorphonuclear leukocyte function in vitro

| Secretion Sample | Phagocytosis (CFU/ml)$^{-3}$ | Bacterial Activity (% kill) | ROS Production$^2$ (1 × 10$^7$) |
| --- | --- | --- | --- |
| HBSS | 1.5$^a$ ± 0.14 | 81.9$^a$ ± 3.5 | 247.6$^a$ ± 19.2 |
| C-0$^1$ | 1.0$^b$ ± 0.10 | 61.6$^{b,c}$ ± 2.5 | 172.1$^c$ ± 13.6 |
| C-7 | 1.0$^b$ ± 0.10 | 57.9$^c$ ± 2.5 | 181.9$^{b,c}$ ± 13.6 |
| C-14 | 1.3$^{a,b}$ ± 0.10 | 69.1$^b$ ± 2.5 | 217.3$^{a,b}$ ± 13.6 |

$^{a,b,c}$Means within each parameter with different superscripts differ (p < 0.05).
$^1$Days preceding calving (C).
$^2$Data expressed as total area under the curve over a 203 min period.

Thus, treatment of mammary neutrophils with recombinant BoIFN-gamma reversed the suppressive effects of mammary secretion, resulting in higher chemiluminescent activity and significantly more bacterial phagocytosis when compared with untreated controls. Results of this study suggested that recombinant BoIFN-gamma may have some immunomodulatory value for the prevention and treatment of bovine mastitis during the periparturient period.

To test this hypothesis, the following experiment was performed.

EXAMPLE 2

The influence of recombinant BoIFN-gamma on the establishment, severity, and duration of experimentally induced *E. coli* mastitis in dairy cattle was tested using the following method.

Experimental Animals

Eight Holstein-Frisian dairy cows were used in this study. These cows were purchased from local dairy producers. Animals arrived at the testing facility during their last trimester of pregnancy and were allowed to acclimate at least one month prior to experimental manipulation. Duplicate quarter foremilk samples were collected aseptically, immediately following arrival to determine infection status of each quarter. Bacteriologically positive quarters were treated with appropriate lactating intramammary antibiotic preparations based on sensitivity tests. The withdrawing time for antibiotic preparations was 72 hours. Animals were resampled approximately one week prior to experimental manipulation to ensure all quarters were free of intramammary infection. Only cows with healthy appearances and normal rectal temperatures, heart rates, and respiration were used in this trial.

Experimental Design

Cows were randomly assigned to one of four treatment groups as outlined in the following table:

TABLE 2

| Group # | Lactation Stage | Treatment* |
| --- | --- | --- |
| 1 | 4 days prepartum | 10$^5$U IFN/qtr at −24 hour |
| 2 | 4 days prepartum | control, no IFN treatment |
| 3 | ≦7 days postpartum | 10$^5$U IFN/qtr at −24 hour |
| 4 | ≦7 days postpartum | control, no IFN treatment |

*Treated cows were intramammarily infused into all four quarters (qtr) with 10$^5$U recombinant BoIFN-gamma at 24 hours prior to experimental challenge. All animals were challenged with approximately 50 CFU of *E. coli* into each quarter.

Mammary quarter secretion samples, sera, and rectal temperatures were collected from each group as outlined in the following table:

TABLE 3

| Group # | Time Post-infusion | | | | | Time Post-challenge | | | | | | | | |
| --- | --- | --- | --- | --- | --- | --- | --- | --- | --- | --- | --- | --- | --- | --- |
| | 0 | 4 | 6 | 8 | 12 | 0 | 4 | 6 | 8 | 12 | 24 | 36 | 48 | 60 |
| 1 | x | | x | | x | x | | x | | x | x | x | x | x |
| 2 | | | | | | x | | x | | x | x | x | x | x |
| 3 | x | x | | x | x | x | x | | x | x | x | x | x | x |
| 4 | | | | | | x | x | | x | x | x | x | x | x |

In groups 1 and 2, all samples were collected again at calving and at 3, 7, and 14 days post-calving. In groups 3 and 4, all samples were collected again at 7 and 14 days post-challenge. During all sampling periods, clinical status of each quarter was recorded. Mammary secretion samples were used to determine infection status and to quantitate concentrations of lactose, fat, total protein, serum albumin, and lactoferrin. Total somatic cell counts, pH, and cytokine levels were also determined. Blood samples were used to determine total and differential cell counts and to quantitate concentrations of total protein, fibrinogen, zinc, iron, and copper.

Quarter milk production was recorded at each milking (8:30 a.m. and 8:30 p.m.). Mammary gland preparation for milking consisted of a prewash with a disinfectant iodine solution and drying with individual paper towels. Prior to each milking, a strip cup was used to observe clinical signs of mastitis in the first few streams of foremilk. Immediately following milking, teats were dipped with a 1% iodophor solution.

At 14 days post-challenge, the cows were slaughtered and approximately 1 cm$^3$ of tissue was obtained from each quarter. Tissue specimens were prepared for both light and electron microscopy.

IFN-gamma infusion

Mammary glands were washed with a disinfectant iodine solution and thoroughly dried with a single service paper towel. A few streams of foremilk were stripped from each quarter. Teat ends were scrubbed with swabs containing 70% isopropyl alcohol. Infusions of IFN-gamma were diluted in 10 ml of sterile saline to a final treatment concentration of 10$^5$ U recombinant BoIFN-gamma per quarter. A sterile 10 ml syringe fitted with an infusion canula was used to deliver the IFN-gamma solution into the streak canal of each quarter. The IFN-gamma infusion was massaged up into the gland cistern and teats were dipped with a disinfectant iodine solution.

Challenge inoculum

*E. coli* was isolated from an acute case of bovine mastitis from the University of Saskatchewan Research Herd. The gram-negative isolates were typed using the API-2pE typing system. Stock cultures of E. coli-V374 were stored at −70° C. in skim milk until needed.

The bacterial challenge was prepared by streaking the stock culture of E. coli-V374 onto Esculin Blood Agar plates containing 5% whole blood. After 48 hours incubation at 37° C., a single colony was used to inoculate 100 ml of Ultra High Temperature (UHT) pasteurized milk and incubated for 12 hours at 37° C. The 12 hour culture was mixed well and a 100 ul aliquot removed to inoculate a second 100 ml of UHT milk. After a 6 hour incubation at 37° C., the culture was serially diluted in 10-fold increments using sterile saline. The colony-forming units (CFU)/ml of each dilution was determined by plate pouring 100 ul of the bacterial suspension onto McConkey agar plates. The dilution containing 50 CFU of E. coli/ml of saline was selected from each trial. Organisms were refrigerated during the time interval between inoculum preparation and actual infusion (approximately 24 hours). Inocula were plated post-challenge to confirm viability counts.

Results

The actual bacterial counts used to challenge each experimental animal were as follows:

| CONTROLS | CFU/QUARTER | IFN-TREATED | CFU/QUARTER |
|---|---|---|---|
| 088 | 50 | 005 | 50 |
| 006[a] | 75 | 007[a] | 75 |
| 033[b] | 30 | 013[b] | 30 |
| 048 | 50 | 040 | 50 |

Animals between treatment groups with the same superscript (a,b) were challenged on the same day with the same bacterial suspension. The efficiency of establishing E. coli mastitis with this model system to mimic acute coliform mastitis as it occurs in the field is summarized in Table 4.

TABLE 4

Rate of experimental intramammary infection in dairy cattle with an E. coli mastitis model

| Average CFU | # Eligible Quarters[1] | # Infected Quarters | % Success |
|---|---|---|---|
| 51 | 15 | 13 | 86 |

[1]Quarters which were not pretreated with recombinant BoIFN-gamma prior to experimental challenge with E. coli Strain V-374

The clinical status of all quarters was recorded immediately prior to experimental challenge and for 26 consecutive observations made at 12 hour intervals. The clinical scores were recorded on a scale from 1 to 5 where: 1 is normal milk with no quarter swelling; 2 is questionable milk but no quarter swelling; 3 is obvious abnormal milk but no quarter swelling; 4 is abnormal milk and swollen and/or tender quarter; and 5 is acute mastitis with systemic involvement.

Figure 4:
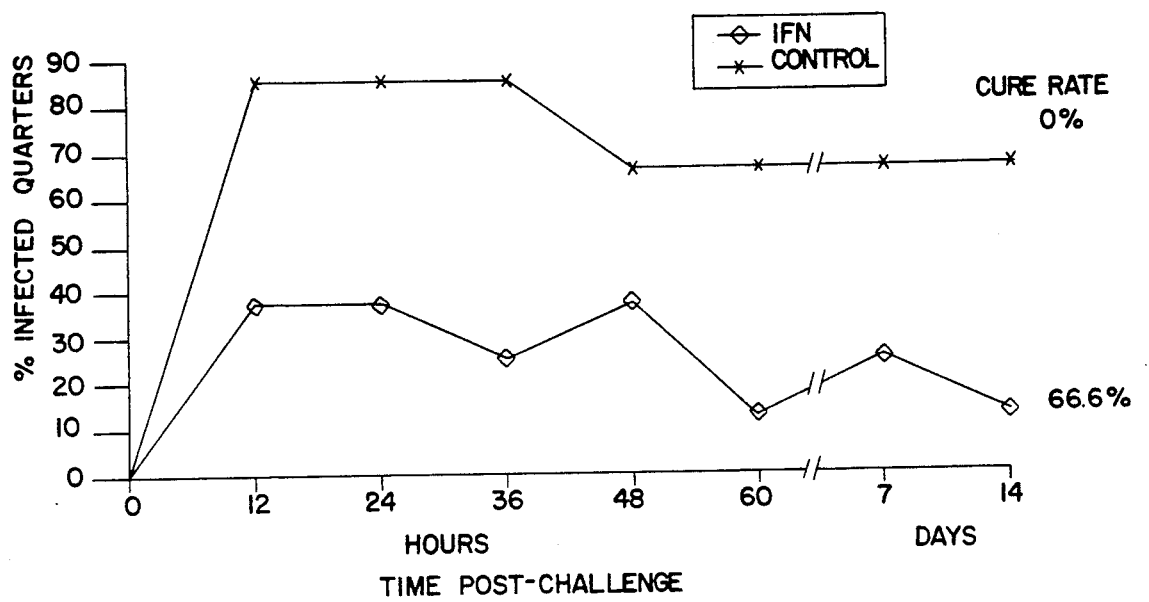
FIG. 4 shows the effect of recombinant bovine IFN-gamma on the rate and duration of experimental *E. coli*-induced bovine mastitis during the immediate portpartum period.
Figure 5:
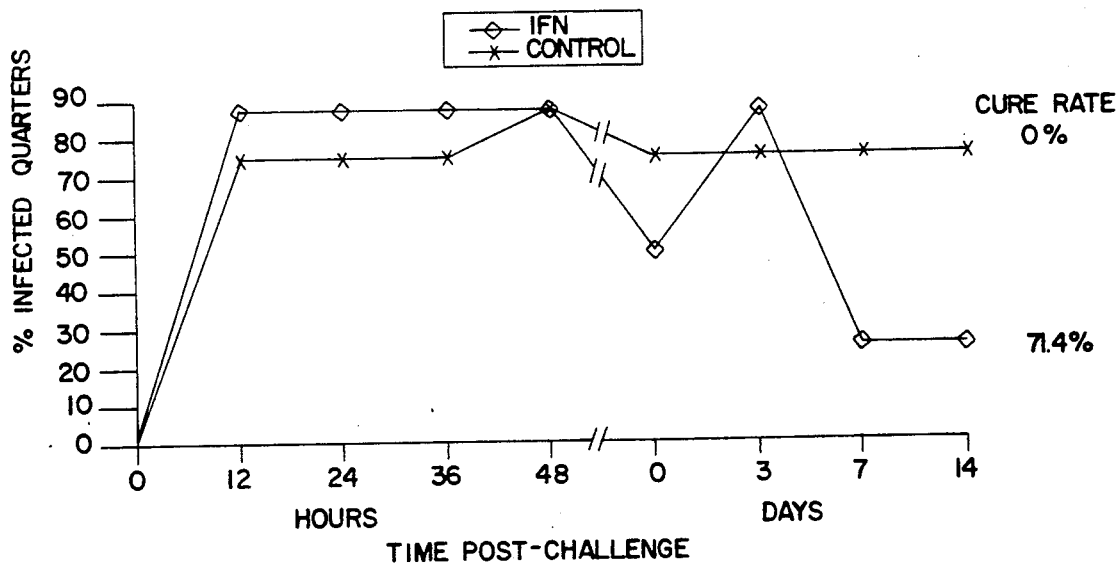
FIG. 5 depicts the effect of IFN-gamma treatment on the rate and duration of experimental *E. coli*-induced bovine mastitis during the prepartum period.

The results of this study can be seen in Tables 5 and 6 and FIGS. 4 and 5.

TABLE 5

Effects of recombinant BoIFN-gamma on the severity of experimental E. coli mastitis

| Treatment Group | # Quarters | Average % Days Clinical[1] | Average Clinical Scores[2] | % Mortality |
|---|---|---|---|---|
| Prepartum | | | | |
| IFN | 8 | 17.79 | 1.32 | 0 |
| CONTROL | 8 | 90.39 | 3.09 | 50 |
| Postpartum | | | | |
| IFN | 8 | 15.39 | 1.33 | 0 |
| CONTROL | 7 | 60.90 | 1.93 | 50 |
| Total | | | | |
| IFN | 16 | 16.59 | 1.33 | 0 |
| CONTROL | 15 | 75.64 | 2.51 | 50 |

[1]Average % days that quarters showed clinical signs of mastitis (i.e., clinical score of 2 or above).
[2]Average clinical score calculated from the 26 consecutive observations following challenge.

Those cows treated with interferon had significantly lower clinical scores, especially in the prepartum period. Furthermore, IFN-treated cows had a 0% mortality rate attributed to mastitis, whereas the control group had a 50% mortality rate (Table 5). IFN-gamma effectively reduced the percentage of infected quarters (Table 6 and FIG. 4), and reduced the rate and duration of experimental E. coli mastitis during the prepartum period (FIG. 5).

TABLE 6

Efficacy of recombinant BoIFN-gamma against experimental E. coli mastitis in dairy cattle

| Treatment Groups | Quarter: # at beginning of trial | Quarter: # infected at end of trial | Quarter: % infected at end of trial | % Reduction |
|---|---|---|---|---|
| Prepartum | | | | |
| IFN | 8 | 2 | 25 | 71.4 |
| CONTROL | 8 | 7 | 87.5 | |
| Postpartum | | | | |
| IFN | 8 | 1 | 12.5 | 85.4 |
| CONTROL | 7 | 6 | 85.7 | |
| Total | | | | |
| IFN | 16 | 3 | 23.1 | 73.4 |
| CONTROL | 15 | 13 | 86.7 | |

Thus, an effective treatment for mastitis has been demonstrated. Although preferred embodiments of the subject invention have been described in some detail, it is understood that obvious variations can be made without departing from the spirit and the scope of the invention as defined by the appended claims.

REFERENCES

Bielefeldt Ohmann, H., and I. A. Babiuk. 1986. Alteration of some leukocyte functions following in vivo and in vitro exposure to recombinant alpha and gamma interferon. J. Interferon Res., 6:123.

Hartmann, P. E. 1973. Changes in the composition and yield of mammary secretion of cows during the initiation of lactation. J. Endocrinol. 59:231.

Hill, A. W. 1981. Factors Influencing the Outcome of Escherichia coli Mastitis in the Dairy Cow. Res. Vet. Sci. 31:107.

Lappegard, K. T., H. B. Benestad, and H. Rollog. 1988. Interferons affect oxygen metabolism in human neutrophil granulocytes. J. Interferon Res. 8:665.

Lawman, M. J. P., M. Campos, H. Bielefeldt Ohmann, and L. A. Babiuk. 1989. Recombinant cytokines and their potential therapeutic value in veterinary medicine. In: Comprehensive Biotech. Pergamon Press, London. In press.

Miller, R. H., U. Emanuelson, and E. Perrson. 1983. Relationships of milk somatic cell counts to daily milk yield and composition. Acta Agric. Scand. 33:209.

Newbold, F. H. S., and F. K. Neave. 1965. The recovery of small numbers of *Staphylococcus aureus* infused into the bovine teat cistern. J. Dairy Res. 32:157.

Nagahata, H., S. Makino, H. Takahashi, and H. Noda. 1988. Assessment of neutrophil function in the dairy cow during the perinatal period. J. Vet. Med. 35:747–751.

Nickerson, S. C. 1989. Immunological aspects of mammary involution. J. Dairy Sci. In press.

Paape, M. J., and N. J. Carlett. 1984. Intensification of milk somatic cell response to intramammary device. Am. J. Vet. Res. 45:1572.

Paape, M. J., W. P. Wergin, A. J. Guidry, and W. D. Schultze. 1981. Phagocytic defense of the ruminant mammary gland. Adv. Exp. Med. Biol. 137:555.

Sordillo, L. M., S. C. Nickerson, and R. M. Akers. 1989. Pathology of *Staphylococcus aureus* mastitis during lactogenesis: relationship with bovine mammary structure and function. J. Dairy Sci. 72:228–240.

Sordillo, L. M., S. C. Nickerson, R. M. Akers, and S. P. Oliver. 1987. Secretion composition during bovine mammary involution and the relationship with mastitis. Int. J. Biochem. 19:1165.

Sordillo, L. M., and S. C. Nickerson. 1988. Morphological changes in the bovine mammary gland during involution and lactogenesis. Am. J. Vet. Res. 49:1112.

Trinchieri, G., and B. Perussia. 1985. Immune IFN: a pleiotropic lymphokine with multiple effect. Immunol. Today. 6:131.

Weber, K., E. Peterhans, and R. Wyler. 1983. The chemiluminescent response of bovine polymorphonuclear leukocytes isolated from milk and blood. Vet. Immunol. Immunopathol. 4:397.

We claim:

1. A method of treating or preventing mastitis in a mammal comprising administering to said mammal by intramammary injection a therapeutically effective amount of interferon.

2. The method of claim 1 wherein said interferon is interferon-gamma.

3. The method of claim 2 wherein said mammal is a cow.

4. The method of claim 3 wherein said interferon-gamma is recombinant bovine interferon-gamma.

5. A method for treating or preventing coliform mastitis in a cow comprising administering to said cow by intramammary injection a therapeutically effective amount of bovine interferon-gamma.

6. The method of claim 5 wherein said injection is given during the prepartum period.

7. The method of claim 5 wherein said injection is given during the postpartum period.

8. The method of claim 5 wherein said interferon-gamma is administered prior to the onset of the infection.

9. The method of claim 5 wherein said interferon-gamma is administered after the onset of infection.

* * * * *